(12) United States Patent
Theobald et al.

(10) Patent No.: US 9,575,492 B1
(45) Date of Patent: Feb. 21, 2017

(54) METHOD AND DEVICE FOR ACCOMMODATING ITEMS

(71) Applicants: Daniel Theobald, Somerville, MA (US); Thomas Allen, Cambridge, MA (US); Josh Ornstein, Arlington, MA (US)

(72) Inventors: Daniel Theobald, Somerville, MA (US); Thomas Allen, Cambridge, MA (US); Josh Ornstein, Arlington, MA (US)

(73) Assignee: VECNA TECHNOLOGIES, INC., Cambridge, MA (US)

( * ) Notice: Subject to any disclaimer, the term of this patent is extended or adjusted under 35 U.S.C. 154(b) by 0 days.

(21) Appl. No.: 14/633,970

(22) Filed: Feb. 27, 2015

Related U.S. Application Data

(63) Continuation of application No. 13/587,098, filed on Aug. 16, 2012.

(51) Int. Cl.
| | |
|---|---|
| *G06F 7/00* | (2006.01) |
| *G05D 1/02* | (2006.01) |
| *B25J 5/00* | (2006.01) |
| *G05B 19/418* | (2006.01) |

(52) U.S. Cl.
CPC ............... *G05D 1/0225* (2013.01); *B25J 5/00* (2013.01); *G05B 19/41895* (2013.01); *G05B 2219/31078* (2013.01); *Y10S 901/01* (2013.01)

(58) Field of Classification Search
USPC .......................................................... 700/228
See application file for complete search history.

(56) References Cited

U.S. PATENT DOCUMENTS

| | | | |
|---|---|---|---|
| 2005/0021187 A1* | 1/2005 | Wang | B25J 5/007 700/259 |
| 2008/0272138 A1* | 11/2008 | Ross | G06F 19/3462 221/1 |
| 2010/0094451 A1* | 4/2010 | Hoganson | B65G 51/44 700/228 |
| 2014/0100690 A1* | 4/2014 | Wurman | G05B 19/4189 700/230 |

* cited by examiner

*Primary Examiner* — Kyle Logan
(74) *Attorney, Agent, or Firm* — Albert J. Brunett

(57) ABSTRACT

A device and method are provided, the method including providing a device capable of at least semi-autonomous operation and enabling the device to autonomously gather at least one item and secure that item against unauthorized access while providing selective authorized access to the item while the item is in possession of the device.

5 Claims, 6 Drawing Sheets

METHOD AND DEVICE FOR ACCOMMODATING ITEMS

RELATED APPLICATIONS

The present application is a continuation of U.S. patent application Ser. No. 13/587,098 filed on Aug. 16, 2012 entitled "Method and Device for Accommodating Items" which is hereby incorporated herein by reference in its entirety.

BACKGROUND OF THE INVENTION

1. Technical Field

The present invention relates generally to devices and, in one aspect, to autonomous and/or semi-autonomous mechanisms that hold and/or transport one or more items.

2. Background Information

Various devices such as vehicles and/or robots have been used for a variety of functions in military, law enforcement and other applications. Such vehicles are typically controlled by an operator, which can limit its uses and effectiveness, and are utilized for surveillance and other light duty activities.

An autonomous or semi-autonomous vehicle, such as a robot or the like, may prove useful in a number of various environments and applications such as, among others, military and law enforcement applications. The complexity and sophistication required from both a mechanical and a software standpoint for safe and accurate performance of such vehicles, however, have been the primary setbacks in their adoption to date in military and law enforcement as well as commercial environments such as, among others, manufacturing, warehousing and medical environments.

It therefore may be desirable to provide an autonomous or semi-autonomous device, such as a vehicle or robot that can safely and accurately perform a number of functions in a variety of settings. It also may be desirable to provide such a device that is capable of safely transporting one or more articles to one or more locations within one or more areas or facilities.

SUMMARY OF THE DISCLOSURE

A device, system and method are provided, the method including providing a device capable of at least semi-autonomous operation and enabling the device to autonomously gather at least one item and secure that item against unauthorized access while providing selective authorized access to the item while the item is in possession of the device.

BRIEF DESCRIPTION OF THE DRAWINGS

The following detailed description will be better understood when read in conjunction with the appended drawings, in which there is shown one or more of the multiple embodiments of the present disclosure. It should be understood, however, that the various embodiments of the present disclosure are not limited to the precise arrangements and instrumentalities shown in the drawings.

DETAILED DESCRIPTION OF THE INVENTION

Figure 1:
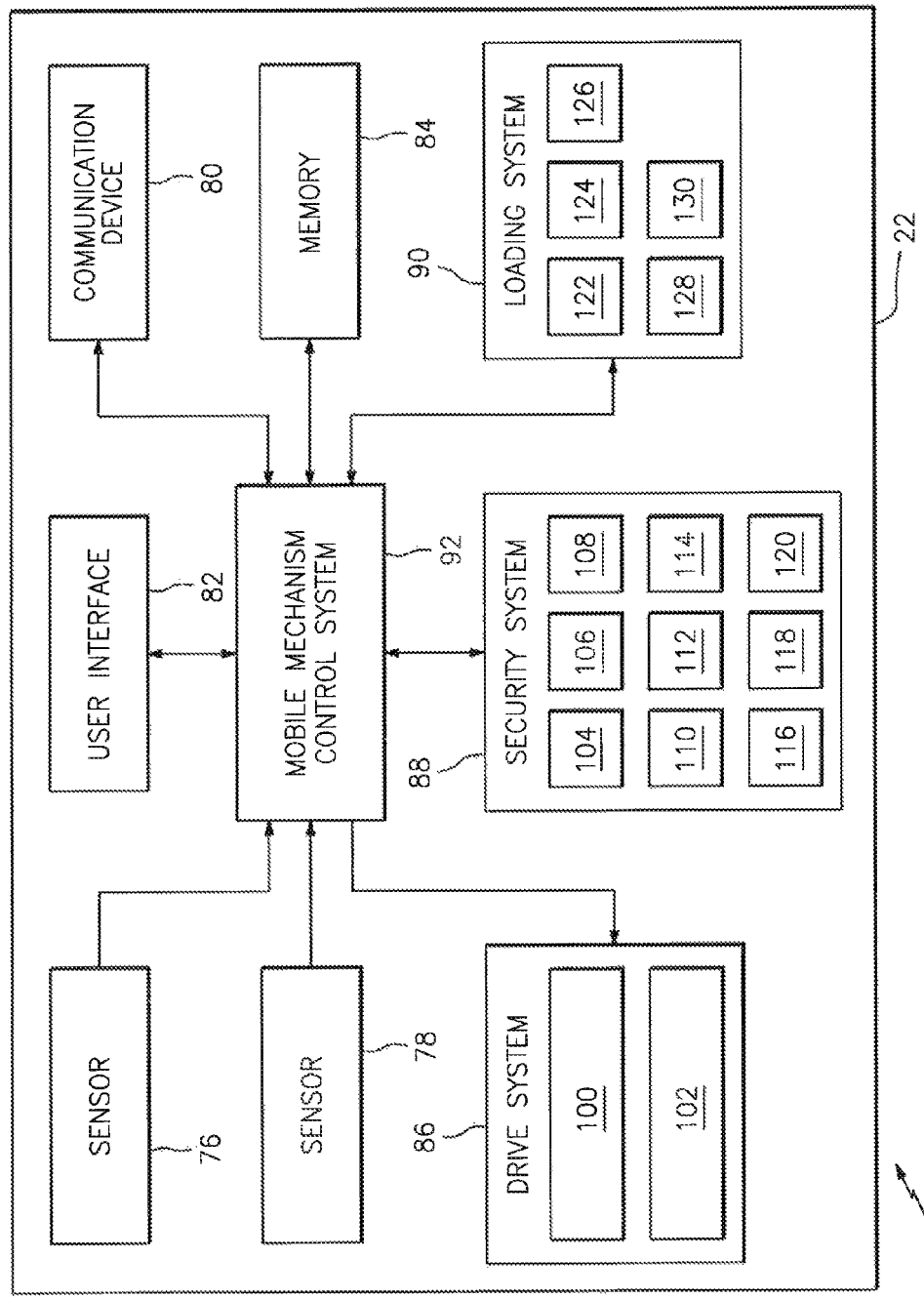
FIG. 1 is a block diagram illustration of an embodiment of an electro-mechanical mobile mechanism according to the present invention.

Embodiments of the present invention will be described below with reference to the accompanying drawings. It should be understood that the following description is intended to describe exemplary embodiments of the invention, and not to limit the invention.

It is understood that the present invention is not limited to the particular module components, analysis techniques, etc. described herein, as these may vary. It is also to be understood that the terminology used herein is used for the purpose of describing particular embodiments only, and is not intended to limit the scope of the present invention. It must be noted that as used herein, the singular forms "a," "an," and "the" include plural reference unless the context clearly dictates otherwise.

Unless defined otherwise, all technical and scientific terms used herein have the same meanings as commonly understood by one of ordinary skill in the art to which this invention belongs. Preferred methods, system components, and materials are described, although any methods and materials similar or equivalent to those described herein can be used in the practice or testing of the present invention.

The design and implementation of autonomous and semi-autonomous electro-mechanical mechanisms such as, for example, vehicles, robots and manipulators is a growing technical area with promising benefits for a variety of industries. Examples of various robotic applications, particularly those with hydraulic systems, are disclosed in U.S. Pat. Nos. 7,902,784; 7,719,222 and 7,348,747, the disclosures of which are hereby incorporated by reference in their entirety. The present disclosure shall govern any discrepancies between it and these patents. It is to be understood, however, that the particular details of the robot, vehicle, tool, actuator, hydraulic system or other apparatus may vary without departing from the teachings of the present invention.

The term "autonomous" or "fully autonomous" may be used to describe an apparatus, system and/or method that may perform one or more tasks without outside control. An autonomous mobile robot, for example, may be configured to perform a task without receiving vectors and/or commands from a human operator during the performance of the task.

The term "semi-autonomous" may be used to describe an apparatus, system and/or method that may perform one or more tasks without continuous outside control. A semi-autonomous mobile robot, for example, may be configured to perform a task utilizing one or more periodic vectors and/or commands from a human operator that bound and/or qualify the performance of the task. The vectors and/or commands, for example, may provide a location of where a task is to be performed, control the scope of the task, etc. It is to be understood, however, that the terms "autonomous", "fully autonomous" and "semi-autonomous" are well known terms in the art and may vary to include definitions other than those provided herein.

An autonomous and/or semi-autonomous, electro-mechanical mobile mechanism (e.g., a vehicle or mobile robot) may be configured to (i) securely hold and/or transport one or more items, and/or (ii) control access to the secured items. The mobile mechanism may securely transport one or more items between a plurality of locations within a military, commercial, and/or consumer environment. The mobile mechanism may also securely hold one or more items (e.g., power sources, etc.) while performing one or more additional tasks within a military, commercial, and/or consumer environment. The additional tasks may include, for example, assisting hospital patients, elderly, disabled and/or otherwise-incapacitated users with activities of daily living (ADL). Examples of activities of daily living may include getting out of bed, getting into and out of a bathtub, getting on and off a toilet, generally navigating around a living quarters, etc. The mobile mechanism of the present invention, however, is not limited to performing any particular type of additional tasks.

In some embodiments, the mobile mechanism may be configured as a mobile robot or robotic vehicle with, for example, one or more manipulators (e.g., robotic arms). In other embodiments, the mobile mechanism may be configured as an unmanned ground vehicle (UGV), and/or an unmanned aerial vehicle (UAV). In still other embodiments, the mobile mechanism may be configured as a rail vehicle (e.g., a train or monorail), and/or a cable vehicle/system. In still other embodiments, the mobile mechanism may be configured as an aquatic vehicle (e.g., a boat), and/or a submersible vehicle. The present invention, however, is not limited to any particular mobile mechanism configuration.

Examples of items that may be securely held and/or transported by the mobile mechanism may include one or more of the following: storage containers (e.g., single or multi-compartment lockboxes), modular components (e.g., removable power sources), regulated and/or over-the-counter pharmaceuticals and/or medications, medical supplies (e.g., needles, surgical tools, linens, etc.), biological and/or contaminated waste (e.g., used needles, bodily fluids, tissue samples, etc.), currency (e.g., cash, coins, checks, bonds, stock certificates, etc.), jewelry, business and/or legal documents, and various other military, business and/or consumer commodities. The present invention, however, is not limited to holding, transporting and/or controlling access to any particular type and/or size of item.

FIG. 1 is a block diagram illustration of an embodiment of a mobile mechanism 20; e.g., a semi-autonomous or autonomous mobile robotic vehicle. The mobile mechanism 20 may include electronics and/or mechanical devices that are configured to (e.g., autonomously or semi-autonomously) operate and/or control one or more mobile mechanism components and/or systems. The electronics and/or mechanical devices and the mobile mechanism components and/or systems may be housed within and/or connected to a mobile mechanism body 22.

Figure 2:
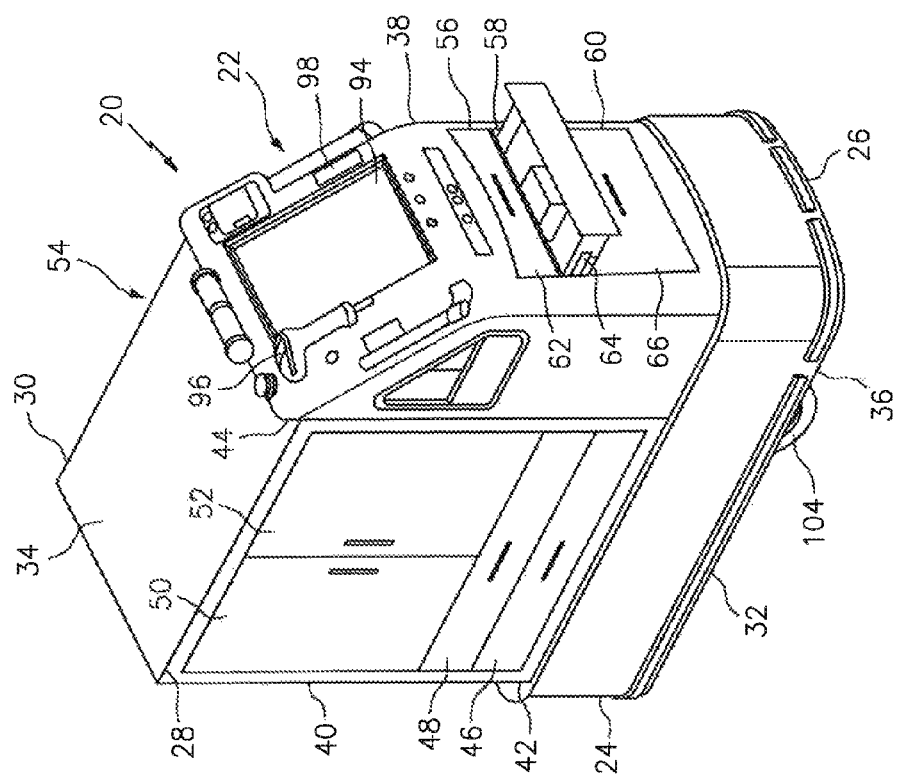
FIG. 2 is a perspective illustration of an embodiment of a mobile mechanism body for the mobile mechanism in FIG. 1.

FIG. 2 is a perspective illustration of an embodiment of the mobile mechanism body 22. The mobile mechanism body 22 extends longitudinally between a first (e.g., aft) end 24 and a second (e.g., forward) end 26. The mobile mechanism body 22 extends laterally between a first side 28 and a second side 30. The mobile mechanism body 22 also extends vertically between a third (e.g., bottom) end 32 and a fourth (e.g., top) end 34.

The mobile mechanism body 22 may include a mobile mechanism base 36, a mobile mechanism console 38, and at least one (e.g., securable) storage container 40. The mobile mechanism base 36 may include an item area first surface 42 (e.g., a cargo deck or bed) that extends, for example, longitudinally from the first end 24 to the mobile mechanism console 38, and laterally between the first side 28 and the second side 30. The mobile mechanism console 38 may include an item area second surface 44 (e.g., a cargo support wall) that extends, for example, laterally between the first side 28 and the second side 30, and vertically from the first surface 42 to the fourth end 34. The storage container 40 may include one or more (e.g., securable) drawers 46 and 48 and one or more (e.g., securable) cabinets 50 and 52.

The mobile mechanism body 22 is configured with one or more securable item areas. The item areas may include, for example, a cargo space 54, one or more component bays 56 and 58, a container bay 60, one or more first storage spaces, and/or one or more second storage spaces. The cargo space 54 may be formed adjacent to the first surface 42 and the second surface 44, and configured to receive and mate with the storage container 40. One or more of the component bays 56 and 58 may be arranged in the mobile mechanism console 38, and configured to receive and mate with one or more respective removable modular components 62 and 64. An example of a removable modular component is a power source (e.g., a battery) that powers the mobile mechanism 20 during operation. The container bay 60 may be arranged in the mobile mechanism console 38, and configured to mate with a removable modular container 66 such as, for example, a drawer, a lockbox, etc. The first storage spaces may be respectively formed within, for example, the drawers 46 and 48. The second storage spaces may be respectively formed within, for example, the cabinets 50 and 52. The number and configuration of the item areas, however, may vary from those described above and illustrated in FIG. 2.

Figure 3:
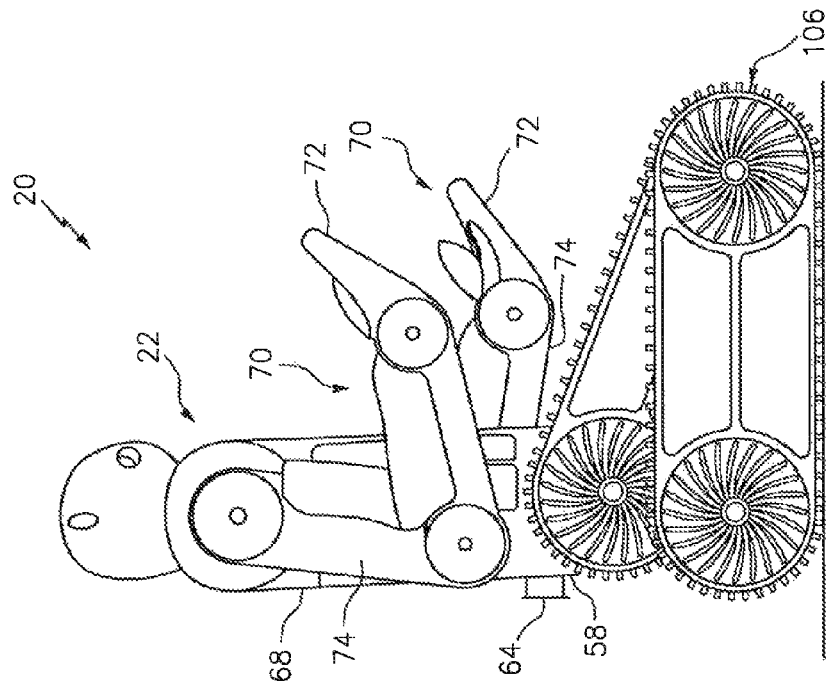
FIG. 3 is a side view illustration of another embodiment of a mobile mechanism body for the mobile mechanism in FIG. 1.

FIG. 3 is a side view illustration of another embodiment of the mobile mechanism body 22. In contrast to the mobile mechanism body configuration shown in FIG. 2, the mobile mechanism body 22 in FIG. 3 may include a mobile mechanism base 68 configured with one or more manipulators 70. One or more of the manipulators 70 may include a (e.g., gripper) end effector 72 connected to a (e.g., single or multi-jointed) arm member 74. Alternative examples of mobile mechanism body and/or manipulator configurations are disclosed in the above-referenced U.S. Pat. Nos. 7,902,784, 7,719,222, and 7,348,747. The present invention, however, is not limited to any particular mobile mechanism body and/or manipulator configurations.

Still referring to FIG. 3, the mobile mechanism body 22 is configured with at least one securable item area such as, for example, a component bay 58. The component bay 58 may be arranged in the mobile mechanism base 68, and configured to receive and mate with a removable modular component 64 such as, for example, a power source (e.g., battery). The number and configuration of the item areas, however, may vary from those described above and illustrated in FIG. 3.

Referring again to FIG. 1, the electronics and/or mechanical devices may include, for example, one or more sensors 76 and 78, a communication device 80 (e.g., a wireless transceiver), a user interface 82, a memory 84, a vehicle drive system 86, an item security system 88, an item loading system 90, and an onboard mobile mechanism control system 92. It is to be understood, however, that the present invention is not to be limited in any way by the aforesaid electronic or mechanical devices, and may include devices and systems other than those specifically described herein as well as any known or future equivalents thereof.

The sensors 76 and 78 may include one or more location and/or proximity sensors configured to spatially locate (e.g., triangulate) the mobile mechanism 20 relative to, for example, its surrounding environment and/or one or more locators (e.g., RF tags, physical landmarks, etc.). Examples of a location and/or proximity sensor may include a global positioning system (GPS) receiver, a radar system, a sonar system, an infrared device, a laser, a camera, a radio transceiver, etc. The present invention, however, is not limited to any particular sensor configurations.

The communication device 80 may include a cellular, satellite and/or radio transmitter, and/or a cellular, satellite and/or radio transmitter receiver.

Referring to FIGS. 1 and 2, the user interface 82 may include one or more input and/or output (I/O) devices, and/or one or more security devices. Examples of an I/O device may include a display screen 94, a speaker, a touch screen, a keypad, and a voice command system with an electro-acoustic transducer (e.g., microphone). Examples of a security device may include a bio-information sensor, palm vein scanner 95, a voice recognition system with an electro-acoustic transducer, a barcode scanner 96, a microchip (or security-chip) reader, a card reader 98, etc. Examples of a bio-information sensor may include an eye retinal sensor or scanner, a fingerprint sensor or scanner, a handprint sensor or scanner (e.g., 95), etc. In some embodiments, at least one of the I/O devices (e.g., the touch screen 94) may also be configured to include at least one of the security devices (e.g., the fingerprint sensor and/or the handprint sensor). The present invention, however, is not limited to any particular I/O device and/or security device configurations.

Referring to FIG. 1, the memory 84 (e.g., a non-transitory computer readable medium) may be configured to store software (e.g., program instructions) for execution by the control system 92. The memory 84 may include a volatile memory and/or a nonvolatile memory. Examples of a volatile memory may include a random access memory (RAM) such as a dynamic random access memory (DRAM), a static random access memory (SRAM), a synchronous dynamic random access memory (SDRAM), a video random access memory (VRAM), etc. Examples of a nonvolatile memory may include a read only memory (ROM), an electrically erasable programmable read-only memory (EEPROM), a computer hard drive, etc. The present invention, however, is not limited to any particular memory configurations.

The drive system 86 may be configured to move the mobile mechanism 20 to various locations around its operating environment. The drive system 86 may include, for example, one or more motorized and/or steerable propulsion devices (e.g., 100 and 102). One example of a propulsion device is a motorized drive wheel 104 as illustrated in FIG. 2. Another example of a propulsion device is a motorized (e.g., robotic and multi-linkage) track system 106 as illustrated in FIG. 3. The present invention, however, is not limited to any particular drive system components and/or configurations.

Referring to FIGS. 1 and 2, the security system 88 may include various electronics and/or mechanical devices that are configured to secure at least one item within at least one item area. The electronics and/or mechanical devices may include, for example, one or more electronically, hydraulically and/or mechanically actuated latches and/or locks (e.g., 104, 106, 108, 110, 112, 114, 116, 118 and 120). The security system 88 may include, for example, one or more latches 104, 106, 108, 110 and 112 that respectively secure (i) the storage container 40 to the first surface 42 and/or the second surface 44, (ii) the modular components 62 and 64 within the component bays 56 and 58, and/or (iii) the modular container 66 within the container bay 60. The security system 88 may also include, for example, one or more locks 114, 116, 118 and 120 that respectively secure the drawers 46 and 48 and/or the cabinets 50 and 52 in a closed position. Alternatively, the security system may include a motor that, for example, closes a drawer (or cabinet) to secure an item therein, and opens the drawer (or cabinet) to provide access to the item. The present invention, however, is not limited to any particular security system components and/or configurations.

The loading system 90 may include various electronics and/or mechanical devices that are configured to move and/or assist in the moving of one or more items into and/or out of the item areas. The electronics and/or mechanical devices may include, for example, one or more electronically, hydraulically, pneumatically and/or mechanically actuated manipulators, motors, end effectors (e.g., grippers, suction devices, electromagnets, etc.), conveyors, slide carriages, etc. The loading system 90 may include, for example, one or more motors 122, 124, 126 and 128 that respectively open one or more of the drawers 46 and 48 and/or one or more of the cabinets 50 and 52 during item loading and unloading, and close the drawers 46 and 48 and/or cabinets 50 and 52 thereafter. The loading system 90 may also include a manipulator 130 that is, for example, configured to (i) extend out of the container bay 60, (ii) grasp or connect to the modular container 66, and (ii) retract the modular container 66 into the container bay 60. The present invention, however, is not limited to any particular loading system components and/or configurations.

Referring to FIG. 1, the control system 92 may be implemented using hardware or a combination of hardware and software. The control system 92 hardware may include one or more processors, analog and/or digital circuitry, etc. The control system 92 is in signal communication (e.g., wirelessly connected or hardwired) with the sensors 76 and 78, the communication device 80, the user interface 82, the memory 84, the drive system 86, the security system 88 and the loading system 90.

Figure 4:
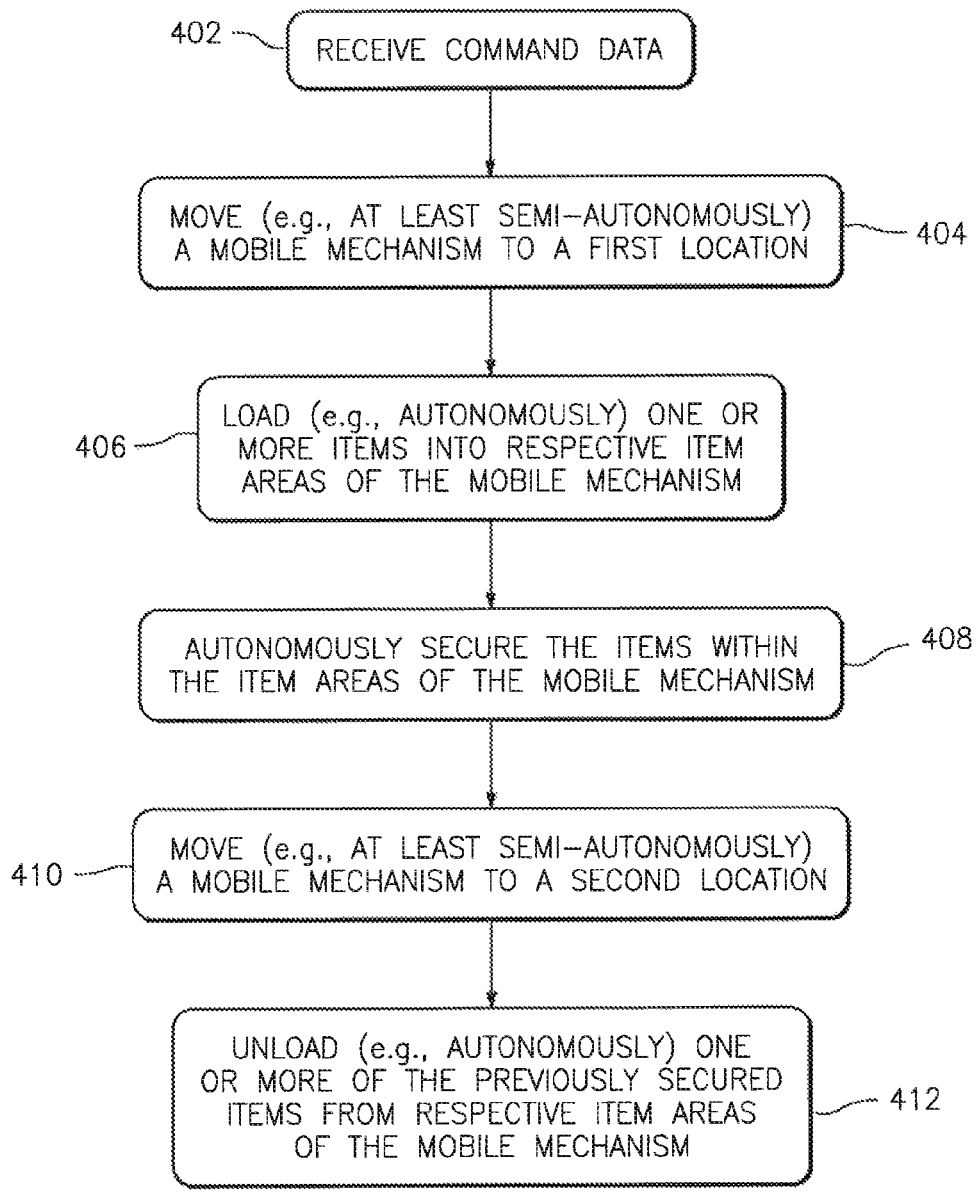
FIG. 4 is a flow diagram of an embodiment of a method for operating the mobile mechanism in FIG. 1.

FIG. 4 is a flow diagram of a method for operating the mobile mechanism 20 illustrated in FIGS. 1 and 2. In step 402, the control system 92 may receive command data (e.g., one or more commands) through the communication device 80 and/or from the user interface 82. The command data may include, for example, scheduling data, inventory data and/or security data. The scheduling data may be indicative of one or more successive (e.g., item pickup and/or drop-off) locations the mobile mechanism 20 is to stop at along a mobile mechanism route. The scheduling data may also be indicative of respective times-of-day and/or dates the mobile mechanism 20 is to stop at the respective locations to pickup and/or deliver the items. The inventory data may be indicative of the types, masses or weights, dimensions, etc. of items to be loaded into and/or unloaded from the mobile mechanism 20 at the respective locations. The security data may be indicative of one or more model security criteria that may be utilized to authorize the pickup and/or drop off of the items. Examples of the model security criteria may include user identification numbers, alphanumeric pass codes, retinal images, fingerprint or handprint images, spoken audio commands and/or passwords, etc. The present invention, however, is not limited to receiving any particular types of command data.

In step 404, the mobile mechanism 20 may move to a first (e.g., pickup) location such as, for example, a hospital pharmacy. The control system 92, for example, may signal the drive system 86 to move the mobile mechanism 20 to the first location based on signals received from the sensors 76 and 78 and/or the scheduling data.

In step 406, one or more items may be respectively loaded into one or more of the item areas. The control system 92, for example, may receive first security criteria through the communication device 80 and/or the user interface 82 from, for example, a first user such as a hospital pharmacist. Examples of the first security criteria may include user identification numbers, alphanumeric pass codes, retinal images, fingerprint or handprint images, spoken audio commands and/or passwords, etc. The first security criteria may be compared to the model security criteria to determine whether the first user is authorized to access one or more of the item areas. Where the first user is determined to be an authorized user, the control system 92 may signal the security system 88 to provide access to the respective item areas. The security system 88, for example, may (i) unlock one or more of the drawers 46 and 48 and/or cabinets 50 and 52, and/or (ii) unlatch the storage container 40, one or more of the modular components 62 and 64, and/or the modular container 66 from the mobile mechanism body 22. The control system 92 may also signal the loading system 90 to open the respective drawers 46 and 48 and/or cabinets 50 and 52.

The first user and/or the loading system 90 may load one or more items into the respective item areas. The first user, for example, may load the drawers 46 and 48 with pharmaceutical supplies. The first user and/or the loading system 90 may also exchange one or more previously secured items for respective replacement items. The loading system 90, for example, may autonomously eject a depleted power source (e.g., 64) from the component bay 58, and autonomously load a replacement (e.g., recharged) power source (e.g., 64) into the component bay 58.

In step 408, the items may be autonomously secured within the respective item areas. The control system 92, for example, may signal the loading system 90 to close the respective drawers 46 and 48 and/or cabinets 50 and 52. The control system 92 may also signal the security system 88 to secure the respective item areas such that unauthorized personnel may not access (e.g., steal, misappropriate, etc.) the secured items while the items are located with the mobile mechanism 20. The security system 88, for example, may (i) lock the drawers 46 and 48 and/or cabinets 50 and 52 shut, and/or (ii) latch the storage container 40, the modular components 62 and 64, and/or the modular container 66 to the mobile mechanism body 22.

In step 410, the mobile mechanism 20 may move to a second (e.g., drop off) location such as, for example, a nurse station, a remote hospital pharmacy, a patient room, etc. The control system 92, for example, may signal the drive system 86 to move the mobile mechanism 20 to the second location based on signals received from the sensors 76 and 78 and/or the scheduling data.

In step 412, one or more of the secured items may be respectively unloaded from one or more of the item areas. The control system 92, for example, may receive second security criteria through the communication device 80 and/ or the user interface 82 from, for example, a second user such as a nurse, a doctor, a patient, etc. Examples of the second security criteria may include user identification numbers, alphanumeric pass codes, retinal images, fingerprint or handprint images, spoken audio commands and/or passwords, etc. The second security criteria may be compared to the model security criteria to determine whether the second user is authorized to access one or more of the item areas. Where the second user is determined to be an authorized user, the control system 92 may signal the security system 88 to provide access to the respective item areas. The security system 88, for example, may (i) unlock one or more of the drawers 46 and 48 and/or cabinets 50 and 52, and/or (ii) unlatch the storage container 40, one or more of the modular components 62 and 64, and/or the modular container 66 from the mobile mechanism body 22. The control system 92 may also signal the loading system 90 to open the respective drawers 46 and 48 and/or cabinets 50 and 52.

The second user and/or the loading system 90 may unload one or more previously secured items from the respective item areas. The second user, for example, may remove the pharmaceutical supplies from the drawers 46 and 48. The second user and/or the loading system 90 may also exchange one or more previously secured items for respective replacement items. The loading system 90, for example, may autonomously eject a depleted power source (e.g., 64) from the component bay 58, and autonomously load a replacement (e.g., recharged) power source (e.g., 64) into the component bay 58.

The aforesaid method may be performed, for example, to securely transport items between a plurality of locations along a mobile mechanism route. The method may also be performed, for example, to exchange worn, broken and/or depleted modular components 62 and 64 (e.g., depleted power sources) for new, repaired and/or recharged modular components 62 and 64 (e.g., recharged power sources) before, after and/or in between performing one or more additional tasks. The mobile mechanism 20 illustrated in FIG. 3, for example, may assist hospital patients, elderly, disabled and/or otherwise-incapacitated users with activities of daily living (ADL), as described above, in between replacing the modular component 64 (e.g., a power source) at the first and/or second locations.

Figure 5:
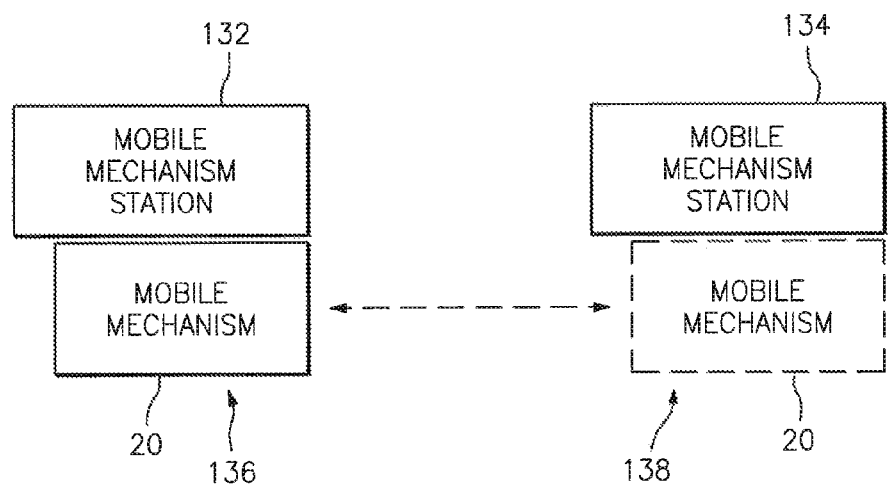
FIG. 5 is a block diagram illustration of an embodiment of a mobile mechanism system according to the present invention.

In some embodiments, for example as illustrated in FIG. 5, the mobile mechanism 20 may also be configured to (e.g., autonomously or semi-autonomously) dock with one or more mobile mechanism stations (e.g., 132 and 134) located at respective locations (e.g., 136 and 138) along the mobile mechanism route. For example, referring to FIGS. 1 and 5, the control system 92 may signal the drive system 86 to move the mobile mechanism 20 to a first (e.g., docking) location 136 adjacent to the first mobile mechanism station 132 based on signals received from the sensors 76 and 78 and/or scheduling data. In some embodiments, the mobile mechanism 20 may contact the mobile mechanism station 132 and/or 134 to physically align and/or mate the mobile mechanism 20 with the mobile mechanism station 132 and/or 134. In other embodiments, the mobile mechanism 20 may be aligned with the mobile mechanism station 132 and/or 134 without such contact where, for example, the control system 92 receives precise location, orientation and/or proximity information from the sensors 76 and 78 and/or the scheduling data.

Figure 6:
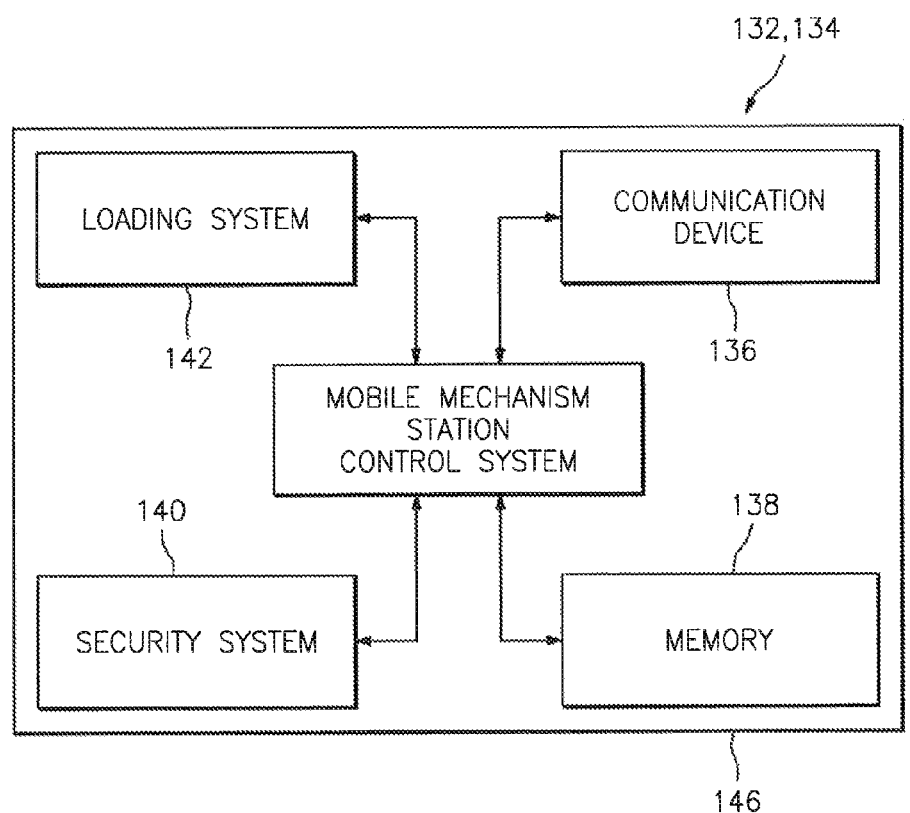
FIG. 6 is a block diagram illustration of an embodiment of a mobile mechanism (e.g., docking) station according to the present invention.

FIG. 6 is a block diagram illustration of an embodiment of the mobile mechanism stations (e.g., 132 and 134). The mobile mechanism stations 132 and 134 may each include electronics and/or mechanical devices that are configured to (e.g., autonomously and/or semi-autonomously) communicate with the mobile mechanism 20, and/or move one or more items into and/or out of the item areas of the mobile mechanism 20. The electronics and/or mechanical devices may include, for example, a communication device 136 (e.g., a wireless transceiver), a memory 138, an item security system 140, an item loading system 142, and a mobile mechanism station control system 144. It is to be understood, however, that present invention is not to be limited in any way by the aforesaid electronic or mechanical devices, and may include devices and system other than those specifically described herein as well as any known or future equivalents thereof.

Figure 7:
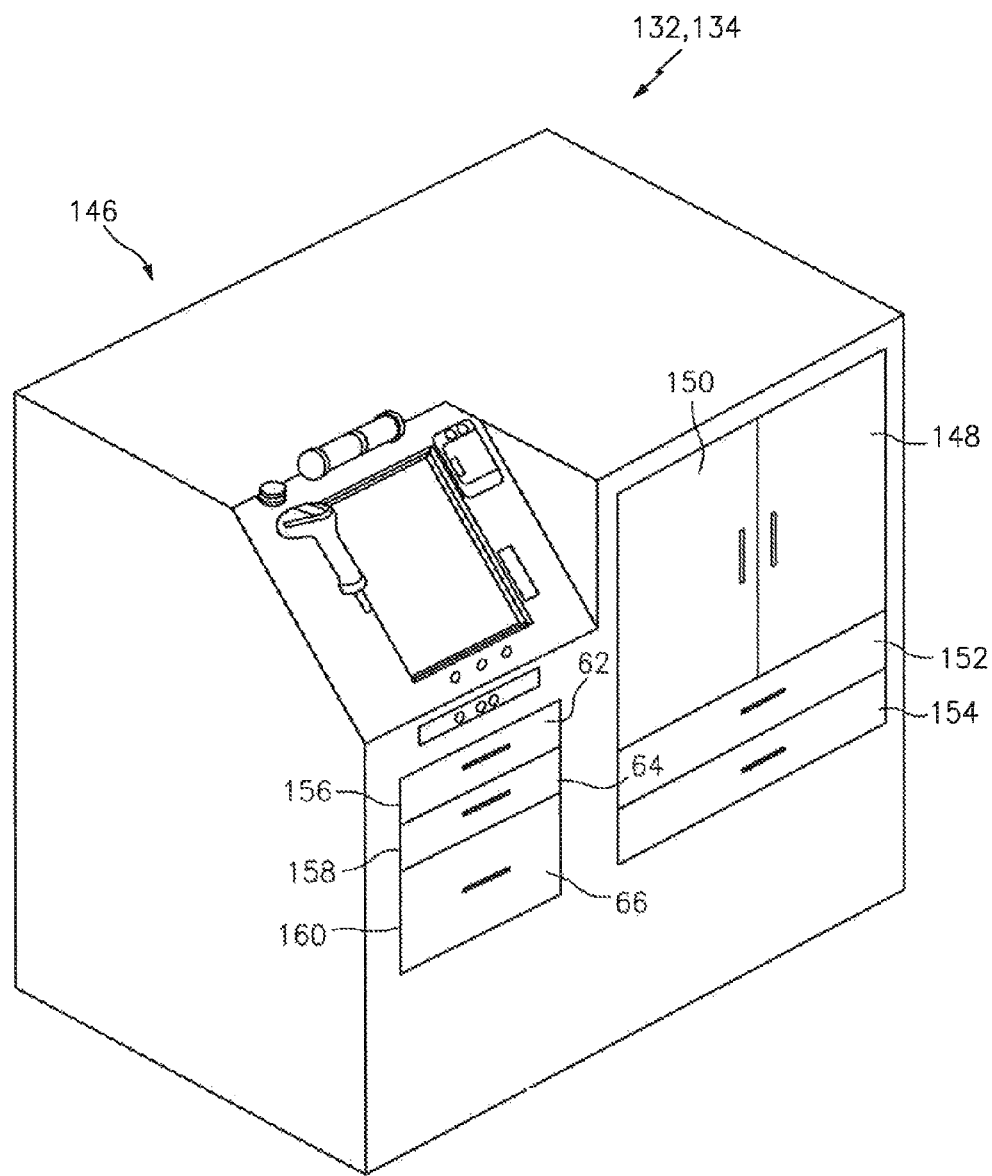
FIG. 7 is a perspective illustration of an embodiment of a station body for the mobile mechanism station in FIG. 6.

The electronics and/or mechanical devices may be configured similar to the afore-described electronics and/or mechanical devices arranged with the mobile mechanism 20. The electronics and/or mechanical devices may be housed within and/or connected to a station body 146. FIG. 7 is a perspective illustration of an embodiment of such a station body 146. The present invention, however, is not limited to any particular electronic, mechanical devices and/or station body configurations.

Figure 8:
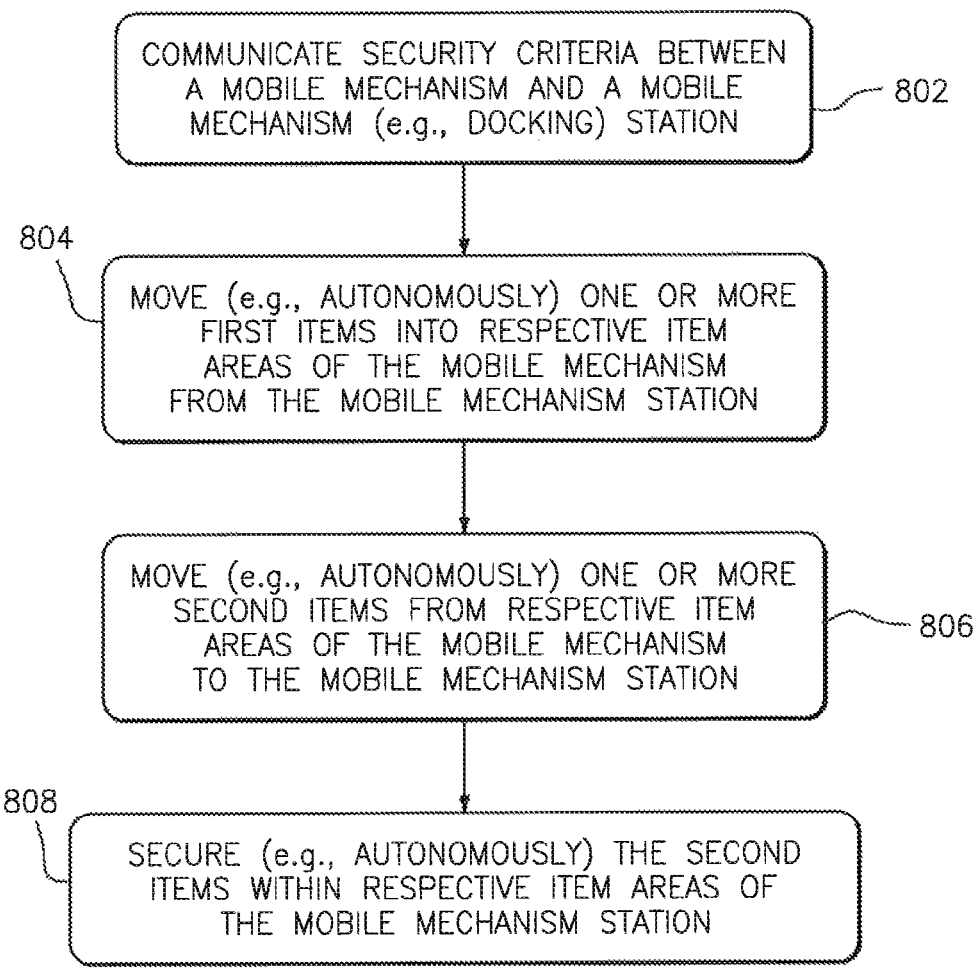
FIG. 8 is a flow diagram of an embodiment of a method for transferring one or more items between the mobile mechanism in FIG. 1 and the mobile mechanism station in FIG. 5.

FIG. 8 is a flow diagram of a method for moving (e.g., loading and/or unloading) one or more items between the mobile mechanism 20 illustrated in FIGS. 1 and 2 and one of the mobile mechanism stations (e.g., 132) illustrated in FIGS. 6 and 7. In step 802, security criteria may be communicated between the communication device 80 and the communication device 136 in order to authorize the loading and/or unloading of one or more items. The mobile mechanism 20, for example, may communicate first security criteria to the mobile mechanism station 132 in order to authorize the moving of one or more items from the mobile mechanism station 132 into respective item areas of the mobile mechanism 20. In another example, the mobile mechanism station 132 may communicate second security criteria to the mobile mechanism 20 in order to authorize the moving of one or more items from the mobile mechanism 20 into respective item areas of the mobile mechanism station 132; e.g., into one or more of the station cabinets 148 and 150, the station drawers 152 and 154 and/or the station bays 156, 158 and 160 (see FIG. 7).

In step 804, one or more first items may be respectively semi-autonomously and/or autonomously loaded into one or more of the item areas of the mobile mechanism 20. The control system 144, for example, may signal the security system 140 to (i) unlock one or more of the station drawers 152 and 154 and/or station cabinets 148 and 150, and/or (ii) unlatch the modular container 66 and/or one or more modular components 62 and 64 from the respective station bays 160, 156 and 158. The control system 144 may subsequently signal the loading system 142 to load one or more first items from the station drawers 152 and 154 and/or station cabinets 148 and 150 into respective drawers 46 and 48 and/or cabinets 50 and 52 of the mobile mechanism 20. The loading system 142 may also (i) eject the modular container 66 and/or one or more of the modular components 62 and 64 from the respective station bays 160, 156 and 158, and (ii) mate the modular container 66 and/or modular components 62 and 64 with respective mobile mechanism bays 60, 56 and 58. Alternatively, the control system 92 may signal the loading system 90 to move the first items from the mobile mechanism station 132 to the mobile mechanism 20.

In step 806, one or more second items may be respectively semi-autonomously and/or autonomously unloaded from one or more of the item areas of the mobile mechanism 20. The control system 92, for example, may signal the security system 88 to (i) unlock one or more of the drawers 46 and 48 and/or cabinets 50 and 52 of the mobile mechanism 20, and/or (ii) unlatch the modular container 66 and/or one or more modular components 62 and 64 from the respective mobile mechanism bays 60, 56 and 58. The control system 92 may subsequently signal the loading system 90 to move one or more second items from the drawers 46 and 48 and/or cabinets 50 and 52 of the mobile mechanism 20 into respective station drawers 152 and 154 and/or station cabinets 148 and 150. The loading system 90 may also (i) eject the modular container 66 and/or modular components 62 and 64 out of the respective mobile mechanism bays 60, 56 and 58, and (ii) mate the modular container 66 and/or modular components 62 and 64 with respective station bays 160, 156 and 158. Alternatively, the control system 144 may signal the loading system 142 to move the second items from the mobile mechanism 20 to the mobile mechanism station 132.

In step 808, the second items may be autonomously secured with the mobile mechanism station 132. The control system 144, for example, may signal the loading system 142 to close the respective station drawers 152 and 154 and/or station cabinets 148 and 150. The control system 144 may also signal the security system 140 to secure the respective items with the mobile mechanism station 132 such that unauthorized personnel may not access the secured items. The security system 140, for example, may (i) lock the station drawers 152 and 154 and/or station cabinets 148 and 150 shut, and/or (ii) latch the modular components 62 and 64, and/or the modular container 66 to the station body 146.

In some embodiments, the mobile mechanism 20 may be configured to dock with a mobile mechanism station where, for example, the control system 92 receives a low power signal. The mobile mechanism station may be (i) at a predetermined location and/or (ii) at the closest location to the mobile mechanism at the time the low power signal is received. A depleted power source in the docked mobile mechanism may be replaced with a charged power source, and the low power signal may be cancelled. The mobile mechanism may subsequently undock with the mobile mechanism station to continue its performance of other task(s).

The mobile mechanism 20 may also be adapted for use with a pneumatic conveying system (not illustrated) that are common in many facilities such as hospitals, factories, drive-up tellers at a bank or the like and retail establishments, among other facilities. In these pneumatic systems, a container is provided, an item to be transported is placed with the interior of the container and the container is placed within a tube of the pneumatic conveying system at an end point or node. Once in the system, the container is transported through the tube to a required destination.

Once at the destination, an operator typically removes the container from the system and the item is extracted. Typically, the item needs to be transported from the end point or node to a final destination within the facility. It is contemplated that the mobile mechanism 20 can readily be utilized to provide this transportation to the final destination by readily acquiring the container at the end point or node, securing the container and transporting that item to an end user or some other type of location, such as a docking station or the like which can be provided with secure access.

It is to be understood that the mobile mechanism 20 can transport one or more items from one docking station to another, from one docking station to a person, from one person to a docking station and from one person to another person. Additionally, a person can interrupt delivery that currently is in progress and may give alternative instructions to the mobile mechanism 20.

Although the description above contains many specific examples, these should not be construed as limiting the scope of the embodiments of the present disclosure but as merely providing illustrations of some of the presently preferred embodiments of this disclosure. Thus, the scope of the embodiments of the disclosure should be determined by the appended claims which include known equivalents and unforeseeable equivalents at the time of filing of this application.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the embodiments of the present disclosure.

What is claimed is:

1. A method of transporting at least one item at a transportation terminal or facility, the method comprising:
    providing a plurality of autonomous mobile robots for operation within and about the transportation terminal or facility, each mobile robot capable of independently navigating within and about the transportation terminal or facility without a need for physical or electro-mechanical guidance devices;
    enabling each mobile robot to capture at least one item from a user at a first location for transporting the item within and about the transportation terminal or facility as desired;
    enabling the user to be identified to the mobile robot via a user input device;
    determining from the identity of the user a desired second location within or about the transportation terminal or facility where the item is to be transported where the second location can vary from item to item;
    securing each item by the mobile robot in at least a portion of each mobile robot from tampering, theft and the elements at least during transportation of the item within and about the transportation terminal or facility;
    transporting each item at least to the second location within or about the transportation terminal or facility;
    enabling queuing of a mobile robot if necessary upon reaching the second location until the item is able to be off loaded at the second location;
    off loading the item from the robot upon reaching the second location within or about the transportation terminal or facility; and
    freeing up the mobile robot to transport other items to and from any other location within or about the transportation terminal or facility.

2. The method of claim 1, further comprising enabling the mobile robot to provide the user with a receipt and the item with an identification tag.

3. The method of claim 1, wherein the item is a piece of luggage and the second location is a security screening station.

4. The method of claim 1, wherein the second location is another item or material handling device and the mobile robot offloads the item to the material handling device.

5. A method of transporting at least one item at a manufacturing facility between successive manufacturing stations, the method comprising:
    providing a plurality of autonomous mobile robots for operation within and about the facility, each mobile robot capable of independently navigating within and about the manufacturing facility without a need for physical or electro-mechanical guidance devices;
    enabling each mobile robot to capture at least one item at a first manufacturing station for transporting the item within and about the manufacturing facility as desired;
    determining a desired second manufacturing station within or about the manufacturing facility where the item is to be transported where the second manufacturing station can vary from item to item;
    securing each item by the mobile robot in at least a portion of each mobile robot from tampering, theft and the elements at least during transportation of the item within and about the manufacturing facility;
    transporting each item at least to the second manufacturing station within or about the manufacturing facility;
    enabling queuing of a mobile robot if necessary upon reaching the second manufacturing station until the item is able to be off loaded at the second manufacturing station;
    off loading the item from the mobile robot upon reaching the second manufacturing station within or about the manufacturing facility; and
    freeing up the mobile robot to transport other items to and from any other manufacturing stations within or about the manufacturing facility.

\* \* \* \* \*